United States Patent [19]

Cotton et al.

[11] Patent Number: 4,683,219
[45] Date of Patent: Jul. 28, 1987

[54] PROCESS FOR PRODUCTION OF A SYNGAS CONVERSION CATALYST

[76] Inventors: Leonard Cotton, 1 Windmill Lane, Ewell, Epsom, Surrey; Barry Nay, 15 Park Place, Woking, Surrey, GU22 7NP; Michael J. Wilcox, Top Flat, 93 Heath Road, Weybridge, Surrey, KT13 8TS, all of England

[21] Appl. No.: 848,401
[22] PCT Filed: Jul. 25, 1985
[86] PCT No.: PCT/GB85/00330
  § 371 Date: Mar. 4, 1986
  § 102(e) Date: Mar. 4, 1986
[87] PCT Pub. No.: WO86/00885
  PCT Pub. Date: Feb. 13, 1986

[30] Foreign Application Priority Data

Jul. 25, 1984 [GB] United Kingdom ............... 8418975

[51] Int. Cl.$^4$ ..................... B01J 23/10; B01J 23/46; B01J 23/58
[52] U.S. Cl. ................... 502/304; 518/715; 518/717
[58] Field of Search ............. 502/302, 304; 518/715, 518/717

[56] References Cited

U.S. PATENT DOCUMENTS 4,172,849 10/1979 Drake ..................... 502/304 X

FOREIGN PATENT DOCUMENTS 50-18380 2/1950 Japan ..................... 502/304
56-81392 7/1981 Japan ..................... 502/304
2119277 11/1983 United Kingdom.

*Primary Examiner*—W. J. Shine

[57] ABSTRACT

A composition for use after reductive activation as a catalyst for the conversion of synthesis gas to hydrocarbons having a carbon number greater than one, which composition has the formula:

$$Ru_a A_b CeO_x$$

wherein
A is an alkali metal,
x is a number such that the valence requirements of the other elements for oxygen is satisfied,
a is greater than zero and less than 1% w/w, based on the total weight of the composition,
b is in the range from zero to 10% w/w, based on the total weight of the composition, and
Ce and O constitute the remainder of the composition,
is produced by the process comprising the steps of:
(A) bringing together in solution soluble salts of the metals ruthenium and cerium and a precipitant comprising a carbonate and/or bicarbonate and/or a hydroxide of an alkali metal or ammonium under conditions whereby there is formed a precipitate comprising ruthenium and cerium in the form of compounds thermally decomposable to their oxides, and
(B) recovering the precipitate obtained in step (A).

Also a process for the conversion of synthesis gas using the catalyst produced as aforesaid, optionally in combination with a zeolite.

14 Claims, No Drawings

PROCESS FOR PRODUCTION OF A SYNGAS CONVERSION CATALYST

The present invention relates to a process for the production of a catalyst for use in the conversion of gaseous mixtures principally comprising carbon monoxide and hydrogen, hereinafter referred to as synthesis gas, to hydrocarbons of carbon number greater than one, in particular to aliphatic hydrocarbons in the gasoline boiling range, and to the use of the catalyst so-produced in the conversion of synthesis gas to the aforesaid hydrocarbons.

The conversion of synthesis gas to hydrocarbons by the Fischer-Tropsch process has been known for many years but the process has only achieved commercial significance in countries such as South Africa where unique economic factors prevail. The growing importance of alternative energy sources such as coal and natural gas has focussed renewed interest in the Fischer-Tropsch process as one of the more attractive direct and environmentally acceptable routes to high quality transportation fuels.

Of the Group VIII metals, ruthenium has long been known to be one of the most active catalysts in the conversion of synthesis gas, the product, at moderate pressures and above, being high molecular weight paraffin waxes and, at low pressures, principally methane. Several recent patent publications, for example U.S. Pats. Nos. 4,042,614; 4,171,320; 4,206,134; 4,413,064 and 4,410,637 and GB-A No. 2119277, describe and claim the formation of different products from synthesis gas using catalysts containing ruthenium as an active component.

U.S. Pat. No. 4,042,614 describes a process for the selective synthesis of olefins from $C_2$ to $C_{10}$ chain length inclusive from synthesis gas using as catalyst ruthenium on a titanium-containing oxide support, wherein said titanium-containing oxide support is selected from the group consisting of $TiO_2$, $ZrTiO_4$, $TiO_2$-carbon, $TiO_2Al_2O_3$, $TiO_2$-$SiO_2$, alkaline earth titanates, rare earth titanates and mixtures thereof.

U.S. Pat. No. 4,171,320 describes a process for the synthesis of olefins of from $C_2$ to $C_5$ chain length inclusive from synthesis gas using as catalyst ruthenium on a support selected from the group consisting of $V_2O_3$, $Nb_2O_5$, $Ta_2O_5$, $Al_2O_3$-$V_2O_3$, $Al_2O_3$-$Nb_2O_5$, $Al_2O_3$-$Ta_2O_5$, $SiO_2$-$V_2O_3$, $SiO_2$-$Nb_2O_5$, $Si_2$-$Ta_2O_5$, $V_2O_3$-carbon, $Nb_2O_5$- carbon, $Ta_2O_5$-carbon, alkaline earth-group VB oxides, alkali metal-Group VB oxides, Group IVB-Group VB oxides and mixtures thereof.

U.S. Pat. No. 4,206,134 describes a process for the enhanced synthesis of $C_2$-$C_4$ olefins with reduced production of methane from synthesis gas using as catalyst ruthenium on a managanese-containing oxide support, wherein said manganese-containing oxide support is selected from the group consisting of MnO, $Al_2O_3$-MnO, $SiO_2$-MnO, MnO-carbon, Group IVB-manganese oxide, Group VB-manganese oxides, rare earth-manganese oxides and mixtures thereof.

U.S. Pat. No. 4,413,064 describes a process for the conversion of synthesis gas to a product high in straight chain paraffins in the diesel fuel boiling range from synthesis gas utilising a catalyst consisting essentially of cobalt, thoria or lanthana and ruthenium on an alumina support wherein said alumina is gamma-alumina, etaalumina or a mixture thereof, said catalyst being prepared by contacting finely divided alumina with (A) an aqueous impregnation slution of a cobalt salt, and
(B) a nonaqueous, organic impregnation solution of a ruthenium salt and a salt of thorium or lanthanum.

U.S. Pat. No. 4,410,637 describes a process for the preparation of a hydrocarbon mixture consisting substantially of $C_5$-$C_{12}$ hydrocarbons from synthesis gas using a catalyst containing one or more of iron, nickel, cobalt, chromium and/or ruthenium and, as a carrier, magadite, a laminar crystalline silicate compound capable of absorbing metal ions or metal salts by intercalation.

The reaction of carbon monoxide and hydrogen on rare earth metal oxide catalysts is described in Chemical Communications, 1983, page 763/764 by Kieffer et al. Catalysts studied were Pd-$La_2O_3$ and Pd-$Dy_2O_3$, both of which were prepared by impregnation.

Finally, GB-A No. 2,119,277 describes a catalyst for the selective synthesis of olefins from a mixture of hydrogen and carbon monoxide or hydrogen and carbon dioxide comprising a ruthenium carbonyl compound deposited on a ceric oxide-containing support. In Example 3 there is disclosed a catalyst prepared by impregnating ceric oxide with an aqueous solution of $RuCl_3 \cdot 3H_2O$ (ruthenium content 0.62% w/w). The impregnated catalyst when used in the conversion of synthesis gas (Run 9) produces an undesirably high methane yield (35.7%) and a low selectivity (1.6%) to desirable olefins.

We have found that ruthenium-containing catalysts produced by coprecipitation can substantially overcome the disadvantages in terms of high methane yield and low selectivity to olefins associated with the prior art impregnated catalysts.

Accordingly the present invention provides a process for the production of a composition for use after reductive activation as a catalyst in the conversion of synthesis gas to hydrocarbons of carbon number greater than one, which composition has the formula:

$$Ru_a A_b CeO_x \qquad (I)$$

wherein

A is an alkali metal, x is a number such that the valence requirements of the other elements for oxygen is satisfied, a is greater than zero and less than 1% w/w, based on the total weight of the composition, b is in the range from zero to 10% w/w. based on the total weight of the composition, and Ce and O constitute the remainder of the composition, which process comprises the steps of:

(A) bringing together in solution soluble salts of the metals ruthenium and cerium and a precipitant comprising a carbonate and/or a bicarbonate and/or a hydroxide of an alkali metal or ammonium under conditions whereby there is formed a precipitate comprising ruthenium and cerium in the form of compounds thermally decomposable to their oxides, and (B) recovering the precipitate obtained in step (A).

It has been found that catalyst differing from catalysts of the invention in the respect that their ruthenium content is greater than 1% w/w tend to produce large quantities of methane, the actual proportion of methane increasing with increasing ruthenium content, whereas catalysts according to the present invention in which the ruthenium content is less than 1% w/w, preferably less than 0.5% w/w, are at the same time both active and selective to hydrocarbons other than methane, and in particular to aliphatic hydrocarbons of carbon number greater than 2, of which $C_5+$ hydrocarbons form a major proportion. Moreover the selectivity to unwanted carbon dioxide can be maintained within acceptable limits, unlike catalysts containing higher ruthenium loadings.

In the formula (I) A is an alkali metal, which is preferably potassium. Preferably the amount b of alkali metal is greater than zero and up to 5% w/w, even more preferably up to 2% w/w.

As regards step (A) of the process, the salts of ruthenium and cerium may suitably be brought together in aqueous solution. Suitably an aqueous solution of the precipitant may be added to an aqueous solution of water soluble salts of the metals, though other variations in the order of addition will be readily apparent to those skilled in the art and may be used if desired. Whilst any soluble salt of ruthenium and cerium may be employed, it will usually be found convenient to use ruthenium in the form of the chloride because this is a commercially available form and cerium in the form of the nitrate, for example cerrous nitrate. Commercially available cerrous nitrate, which contains rare earth metals other than cerium, may be employed if desired.

The precipitant in step (A) is a carbonate and/or a bicarbonate and/or a hydroxide of an alkali metal. Instead of using a pre-formed carbonate or bicarbonate it is possible to use the precursors of these salts, for example a water soluble salt and carbon dioxide. Alternatively, urea, which is thermally decomposable to carbon dioxide and ammonia, may be used. In any event, b in the aforesaid formula (I) will have a value greater than zero, which value may be adjusted if desired by washing or addition of further alkali metal compound. Alternatively, ammonium carbonate and/or bicarbonate and/or hydroxide may be employed as the precipitant, in which case the value of b in the catalyst as initially produced will be zero, though this value may subsequently be adjusted if desired by addition of alkali metal.

Suitably the soluble salts of the metals ruthenium and cerium may be brought together at a temperature in the range from 0° to 100° C. In one preferred embodiment of the invention the temperature is suitably in the range from 60° to 100° C., preferably from 80° to 100° C. In another preferred embodiment the temperature is suitably below 50° C., preferably below 30° C., for example ambient temperature.

Addition of the precipitant to the solution of metal salts causes the initally low pH of the mixture to rise. It is desirable in the preparation of catalysts according to the invention that the final pH of the mixture is greater than 6, preferably in the range from 6 to 10, even more preferably in the range from 8 to 10. The precipitant may be added until a pH in the aforesaid range is achieved, whereupon the addition of further precipitant may be discontinued, thereby arresting the rise in the pH. In order to improve the homogeneity of the catalyst it is preferred to agitate the mixture during precipitation, suitably by mechanical stirring. After precipitation, it is preferred to maintain the mixture at a temperature close to boiling for a period of at least 15 minutes, preferably whilst stirring, for the purpose of completing the precipitation.

The amounts of the ruthenium and cerium salts and precipitant employed should be such as to satisfy the stoichiometric relationships in the formula (I). Alternatively, the alkali metal content of the composition may be supplemented by further addition thereof, or reduced, for example by washing, at any subsequent point in the preparative process.

In step (B) the precipitate obtained in step (A) is recovered. This may suitably be accomplished by filtration but other methods for separating solids from liquids, for example centrifugation, may be employed. After recovery it is preferred to wash the precipitate, suitably with water, so as to remove unwanted residual soluble matter. It is also preferred to dry the precipitate, suitably at an elevated temperature below 180° C., for example about 120° to 150° C.

Thermally decomposable compounds comprised in the precipitate recovered in step (B) are preferably thermally decomposed in a discrete step (C). This may suitably be accomplished by heating the precipitate, suitably in a non-reducing atmosphere, for example a stream of inert gas, such as nitrogen, or an oxygen-containing gas such as air, at a temperature suitably in the range from 250° to 600° C.

In order to convert the composiion of formula (I) into a catalyst for use in the conversion of syngas to hydrocarbons having a carbon number greater than 1, it is generally necessary to reductively activate the composition, suitably by contact at elevated temperature with a reducing gas, for example hydrogen, carbon monoxide or mixtures thereof. A suitable reducing gas is for example hydrogen which may be diluted with an inert gas such as nitrogen. Typically, the conditions employed may suitably be a pressure in the range from 1 to 100 bar and a temperature in the range from 150° to 350° C. for a period of up to 24 hours or longer. Reductive activation may be effected as a discrete step prior to use as a catalyst for the conversion of synthesis gas or it may be incorporated into the synthesis gas conversion process.

Those skilled in the art will readily appreciate that it may be possible to combine the thermal decomposition step and the reductive activation step into a single step under certain circumstances.

It is believed that coprecipitated catalysts differ fundamentally from impregnated catalyst and that this difference is reflected in their catalytic performance.

The present invention also provides a process for the production of hydrocarbons having a carbon number greater than one from synthesis gas which process comprises contacting synthesis gas with a catalyst comprising the reductively activated composition having the formula (I) at a temperature in the range from 190° to 400° C. and a pressure in the range from 0 to 100 bar.

Reductive activation of the composition of formula (I) may be conducted either as a separate step outside the syngas conversion reactor, as a discrete step within the syngas conversion reactor prior to syngas conversion or within the syngas conversion reactor under syngas conversion conditions.

As is well known in the art synthesis gas principally comprises carbon monoxide and hydrogen and possibly also minor amounts of carbon dioxide nitrogen and other inert gases depending upon its origin and degree of purity. Methods for preparing synthesis gas are established in the art and usually involve the partial oxidation of a carbonaceous substance, e.g. coal. Alternatively, synthesis gas may be prepared, for example by the caalytic steam reforming of methane. For the purpose of the present invention the carbon monoxide to hydrogen ratio may suitably be in the range from 2:1 to 1:6. Whilst the ratio of the carbon monoxide to hydrogen in the synthesis gas produced by the aforesaid proceses may differ from these ranges, it may be altered appropriately by the addition of either carbon monoxide or hydrogen, or may be adjusted by the so-called shift reaction well known to those skilled in the art.

In a modification of the process for the production of hydrocarbons, there may be combined with the catalyst an inert material, for example silica. It is preferred, however, to combine the catalyst with a zeolite.

The zeolite may be either physically admixed with the composition to form an intimately mixed bed or may be separate therefrom, for example in the form of a split bed, the zeolite forming one portion of the bed and the catalyst another. In the case of a physical admixture, the zeolite may be mixed with the composition either before or after reductive activation. Alternatively, the coprecipitation (step A) in the process for producing the composition of formula (I) may be performed in the presence of the zeolite, particularly when the precipitant is ammonium carbonate and/or bicarbonate and/or hydroxide.

A suitable zeolite is an MFI-type zeolite, for example ZSM-5 as described in U.S. Pat. No. 3,702,886. It is preferred to use the hydrogen form of the zeolite which may be obtained by acid exchange or by thermal decomposition of the ammonium-exchanged form of the zeolite. Preferably the alkali metal-free composition (b in the formula (I)=0) is modifed by combination with the zeolite. Suitably the ratio of the number of parts by volume of catalyst composition to the number of parts by volume of the zeolite may be in the range from 5:1 to 1:5, preferably about 2:1. Combination with a zeolite can improve the selectively to gasoline range paraffinic hydrocarbons.

The temperature is preferably in the range from 250° to 350° C. and the pressure is preferably in the range from 10 to 50 bars. The GHSV may suitably be in the range from 100 to 5000 $h^{-1}$.

The process may be carried out batchwise or continuously in a fixed bed, fluidised bed or slurry phase reactor.

The invention will now be further illustrated by the following Examples.

CATALYST PREPARATION (a) By Coprecipitation at Elevated Temperature

EXAMPLE 1—COMPOSITION A (0.5% Ru/Kx/CeO$_2$)

Cerous nitate (68.8 g:0.16 mol) was dissolved in deionised water (300 ml). To this was added a solution of ruthenium (III) chloride (0.31 g:0.001 mol) dissolved in hot deionised water (30 ml). The solution was heated to 80° C. with stirring and then a solution of potassium carbonate (160 g) in deionised water (200 ml) was added dropwise until pH 8.3 was attained (ca 60 ml). The mixture was heated at ca. 90° C. with stirring for 0.5 h. The grey precipitate was filtered, washed twice by slurrying with deionised water (2×500 ml) and dried in air at 125° C. for 17.0 h.

EXAMPLE 2—COMPOSITION B (0.5% Ru/Kx/CeO$_2$)

The procedure of Example 1 was repeated.

EXAMPLE 3—COMPOSITION C

A 0.5% Ru/Kx/CeO$_2$ catalyst was prepared by the procedure of Example 1 and a further 1% w/w potassium added thereto.

EXAMPLES 4 TO 6—COMPOSITIONS D TO F

Cerous nitrate (68.8% g; 0.16 mol) was dissolved in deionised water (200 ml). To this was added a solution of ruthenium (III) chloride (0.31 g; 0.001 mol) dissolved in hot deionised water (30 ml). The solution was heated to ca 80°-85° C. with rapid stirring and then a solution of potassium carbonate (150 g) in deionised water (1000 ml) was added at a rate of 25 ml/min until pH 8.5-9.5 was attained (ca 225 ml). The mixture was heated to boiling point and boiled for 12 minutes. The heat was then removed and stirring was continued for a further 20 minutes. The precipitate was left to stand in solution overnight and then filtered, washed by slurrying twice with deionised water (2×300 ml) and then dried in air at 150° C. overnight (17.0 h).

(b) By Coprecipitation at Low Temperature

EXAMPLE 7—COMPOSITION G

Cerous nitrate (68.8 g; 0.16 mol) was dissolved in deionised water (300 ml). To this was added a solution of ruthenium (III) chloride (0.34 g; 0.011 mol) dissolved in hot deionised water (30 ml). A solution of potassium carbonate (75 g) in deionised water (500 ml) was added at room temperature dropwise with vigorous stirring until pH 9.5 was attained. The mixture was stirred for a further 15 minutes to ensure complete reaction. The resulting grey precipitate was filtered, washed twice by slurrying with deionised water (2×300 ml) and dried in air at 120° C. for 17 hours.

(c) Thermal Decomposition/Reductive Activation to Produce the Catalyst (i) Catalysts A to G The compositions were pretreated as follows:

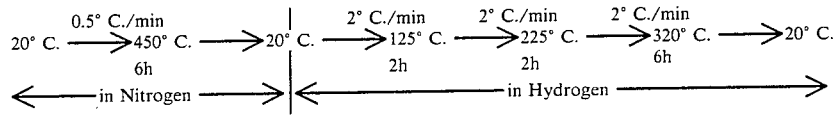

CATALYST TESTING

EXAMPLE 8

Catalyst A was sieved to BSS 8-20 mesh and loaded into a fixed bed reactor. The catalyst was reduced in the reactor under a slow stream of hydrogen at 225° C. for 17 hours. Synthesis gas was then introduced into the reactor, the pressure adjusted to 20 bar and the run started.

The reaction conditions employed and the results obtained are shown in the Table.

EXAMPLE 9

Example 8 was repeated except that Catalyst A was replaced by Catalyst B.

EXAMPLE 10

Example 8 was repeated except that Catalyst A was replaced by Catalyst C.

EXAMPLE 11

Example 8 was repeated except that Catalyst A was replaced by Catalyst D.

EXAMPLE 12

Example 8 was repeated except that Catalyst A was replaced by Catalyst E.

EXAMPLE 13

Example 8 was repeated except that Catalyst A was replaced by Catalyst F.

EXAMPLE 14

Example 8 was repeated except that Catalyst A was replaced by Catalyst G.

EXAMPLE 15

Example 8 was repeated except that Catalyst A was replaced by a split bed consisting of a catalyst prepared in the manner of Catalyst A (6.0 ml) forming the top portion thereof and an H-MFI zeolite (4.0 ml) forming the bottom portion thereof.

EXAMPLE 16

Example 15 was repeated except that the temperature was increased.

The reaction conditions employed and the results obtained by Examples 8 to 16 are shown in the Table.

TABLE

| | | | | CO:$H_2$ molar ratio = 1:2 Pressure = 20 bar | | | | | |
|---|---|---|---|---|---|---|---|---|---|
| | | Temp. | GHSV | CO conversion | Molar Selectivity (%) | | | | $C_5^+$ Productivity |
| Example | Catalyst | (°C.) | ($h^{-1}$) | (%) | $CO_2$ | $CH_4$ | $C_2$-$C_4$ | $C_5^+$ | (g/liter catalyst/h) |
| 8 | A | 357 | 1250 | 71 | 18 | 8 | 15 | 58 | 90 |
| 9 | B | 385 | 5002 | 38 | 25 | 16 | 24 | 35 | 124 |
| 10 | C | 323 | 2501 | 36 | 17 | 12 | 20 | 51 | 81 |
| | | 347 | 2501 | 59 | 19 | 15 | 22 | 43 | 145 |
| 11 | D | 349 | 2500 | 80 | 17 | 9 | 22 | 52 | 216 |
| 12 | E | 345 | 2500 | 68 | 16 | 8 | 18 | 57 | 202 |
| 13 | F | 335 | 2500 | 63 | 14 | 8 | 21 | 58 | 190 |
| 14 | G | 345 | 2520 | 90.9 | 12 | 8 | 19 | 61 | 272 |
| 15 | | 330 | 1500 | 43 | 20 | 5 | 19 | 56** | 75 |
| 16 | | 340 | 1500 | 53 | 17 | 11 | 23 | 49** | 81 |

*Oxygenates not included in molar selectivity
**$C_5$ to $C_{11}$ + light aromatics (BTX)

We claim:

1. A process for the production of a composition for use after reductive activation as a catalyst in the conversion of synthesis gas to hydrocarbons of carbon number greater than one, which composition has the formula:

$$Ru_aA_bCeO_x \quad (I)$$

wherein
A is an alkali metal,
x is a number such that the valence requirements of the other elements for oxygen is satisifed,
a is greater than zero and less than 1% w/w, based on the total weight of the composition,
b is in the range from zero to 10% w/w, based on the total weight of the composition, and
Ce and O constitute the remainder of the composition, which process comprises the steps of:
(A) bringing together in solution soluble salts of the metals ruthenium and cerium and a precipitant comprising a carbonate and/or a bicarbonate and/or a hydroxide of an alkali metal or ammonium under conditions whereby there is formed a precipitate comprising ruthenium and cerium in the form of compounds thermally decomposable to their oxides, and
(B) recovering the precipitate obtained in step (A).

2. A process according to claim 1 wherein the ruthenium content (a in the formula I) is less than 0.5% w/w.

3. A process according to either claim 1 or claim 2 wherein the amount (b) of alkali metal (A) is greater than zero and up to 5 w/w.

4. A process according to claim 3 wherein the alkali metal (A) is potassium.

5. A process according to claim 1 wherein the salts of ruthenium and cerium are brought together in aqueous solution.

6. A process according to claim 1 wherein the salts of ruthenium and cerium are brought together at a temperature in the range 0° to 100° C.

7. A process according to claim 6 wherein the temperature is in the range from 80° to 100° C.

8. A process according to claim 6 wherein the temperature is below 30° C.

9. A process according to claim 1 wherein in step (A) the final pH is in the range from 6 to 10.

10. A process according to claim 1 wherein thermally decomposable compounds comprised in the precipitate recovered in step (B) are thermally decomposed in a discrete step (C) comprising heating the precipitate at a temperature in the range from 250° to 600° C.

11. A process according to claim 10 wherein the precipitate is heated in a stream of nitrogen or air.

12. A process according to claim 1 wherein the composition of formula (I) is reductively activated by contact at elevated temperature with a reducing gas.

13. A process according to claim 12 wherein the reducing gas comprises hydrogen.

14. A process according to either claim 12 or claim 13 wherein reductive activation is effected at a pressure in the range from 1 to 100 bar and a temperature in the range from 150° to 350° C. for a period of up to 24 hours.

* * * * *

UNITED STATES PATENT AND TRADEMARK OFFICE
CERTIFICATE OF CORRECTION

PATENT NO. : 4,683,219
DATED : July 28, 1987
INVENTOR(S) : Leonard Cotton et al

It is certified that error appears in the above-identified patent and that said Letters Patent is hereby corrected as shown below:

Col. 1, line 41, "$O_2Al_2O_3$" should read
-- $O_2-Al_2O_3$ --

Col. 5, line 61, "nitate" should read -- nitrate --

Col. 6, line 34, "(0.34 g; 0.011 mol)" should read
-- (0.34 g; 0.0011 mol) --

Claim 3, line 19 "up to 5 w/w" should read
-- up to 5% w/w --

Signed and Sealed this

First Day of December, 1987

Attest:

DONALD J. QUIGG

Attesting Officer

Commissioner of Patents and Trademarks